United States Patent [19]

Pendergrass, Jr.

[11] Patent Number: 5,395,047
[45] Date of Patent: Mar. 7, 1995

[54] REPOSITIONABLE DEVICE FOR DELIVERY OF VOLATILE MATERIALS

[75] Inventor: Daniel B. Pendergrass, Jr., Mendota Heights, Minn.

[73] Assignee: Minnesota Mining and Manufacturing Company, St. Paul, Minn.

[21] Appl. No.: 66,720

[22] Filed: May 24, 1993

[51] Int. Cl.⁶ .................................................. A61L 9/12
[52] U.S. Cl. .................................. 239/56; 239/34; 428/905
[58] Field of Search ................ 239/34, 36, 53, 55, 239/56; 428/905

[56] References Cited

U.S. PATENT DOCUMENTS

| | | |
|---|---|---|
| Re. 32,513 | 10/1987 | Seaber et al. ............... 239/34 X |
| 2,303,073 | 11/1942 | Brown . |
| 2,615,754 | 10/1952 | Lindenberg ................ 239/56 X |
| 2,626,833 | 1/1953 | Valentine ..................... 239/56 |
| 2,691,615 | 10/1954 | Turner et al. . |
| 2,988,284 | 6/1961 | Smith ........................... 239/54 |
| 3,685,734 | 8/1972 | Paciorek et al. ............ 239/56 |
| 3,691,140 | 9/1972 | Silver . |
| 3,844,478 | 10/1974 | Davis . |
| 3,951,622 | 4/1976 | Wilk . |
| 4,105,813 | 8/1978 | Mizuno ...................... 239/55 X |
| 4,145,001 | 3/1979 | Weyenberg et al. ......... 239/56 |
| 4,158,440 | 6/1979 | Sullivan et al. ............. 239/56 X |
| 4,197,271 | 4/1980 | Fenstermaker et al. ..... 239/56 X |
| 4,277,024 | 7/1981 | Spector ........................ 239/36 |
| 4,283,011 | 8/1981 | Spector ........................ 239/36 |
| 4,345,716 | 8/1982 | Armstrong et al. .......... 239/56 |
| 4,356,969 | 11/1982 | Obermayer et al. ........ 239/56 X |
| 4,515,703 | 5/1985 | Haq . |
| 4,529,124 | 7/1985 | Sullivan et al. ............. 239/56 |
| 4,605,165 | 8/1986 | Van Loveren et al. ..... 236/56 X |
| 4,655,767 | 4/1987 | Woodard et al. . |
| 4,744,514 | 5/1988 | Gadoua ....................... 239/36 |
| 4,874,129 | 10/1989 | DiSapio et al. .............. 239/36 |
| 5,071,704 | 12/1991 | Fischel-Ghodsian ...... 428/905 X |
| 5,230,867 | 7/1993 | Kunze et al. .............. 428/905 X |

FOREIGN PATENT DOCUMENTS

| | | |
|---|---|---|
| 274707 | 4/1967 | Australia ..................... 239/55 |
| 0019010 | 11/1980 | European Pat. Off. . |
| 0317658 | 5/1989 | European Pat. Off. . |
| 0348970 | 1/1990 | European Pat. Off. . |

*Primary Examiner*—William Grant
*Attorney, Agent, or Firm*—Gary L. Griswold; Walter N. Kirn; Dale A. Bjorkman

[57] ABSTRACT

A device for delivery of volatile materials comprising a volatile material delivery layer, a support layer and a repositionable adhesive layer. Devices so constructed may be applied to any desired substrate without fear of harming the surface of the substrate.

14 Claims, 2 Drawing Sheets

REPOSITIONABLE DEVICE FOR DELIVERY OF VOLATILE MATERIALS

FIELD OF THE INVENTION

This invention relates to a device for delivery of volatile materials. More specifically, this invention relates to a repositionable device for delivery of volatile materials.

BACKGROUND OF THE INVENTION

Various devices have been described in the past for delivery of volatile materials to the air for purposes of providing a pleasant odor or delivering an active ingredient such as insect repellent or medicine. U.S. Pat. No. 3,575,345 to Buck describes a deodorizer dispenser for delivery of a perfume to the atmosphere. The dispenser is provided with a strong adhesive to position the dispenser in a discrete location. The adhesive is specifically selected to be strong, so that its removal (for example, by children) is difficult. See column 2, lines 22-29.

U.S. Pat. No. 3,896,995 to Lelicoff discloses an insect repellent assembly that is to be placed on a user's garment. The assembly is provided with a film of pressure-sensitive adhesive, which removably holds the assembly on a desired portion of the user or user's garment. There is no discussion of the nature of the pressure-sensitive adhesive used in the assembly, and no indication that the assembly is repositionable. Because fabric of garments usually readily releases fibers on removal of adhesive tape adhered thereto and oils on the skin similarly transfer to adhesive tape, it is expected that such devices are not repositionable once removed from the intended substrate taught in this reference.

Products currently on the market that incorporate an adhesive to mount room air freshener devices on a wall or similar surface all utilize aggressive adhesives that tend to damage or mar the surface on which the product is mounted when the product is removed.

SUMMARY OF THE INVENTION

The present invention provides a device for delivery of volatile materials comprising a volatile material delivery layer, a support layer and a repositionable adhesive layer. Devices so constructed may be applied to any desired substrate without fear of harming the surface of the substrate. Until now, there has been no satisfactory method of providing delivery of volatile materials to a local atmosphere without having a clumsy gel or solid dispenser that may be knocked over, or a conspicuous container that is aggressively adhered to a surface.

Preferably, the delivery of volatile materials is accomplished using a slim and discrete delivery device that may be conveniently applied to a desired substrate and that is capable of sticking in place for at least as long as the volatile material is functionally emanating from the device. The device is repositionably adhered to the substrate, so that it may be moved from one location to another without diminishing the continued use of the device. Repositionability is particularly advantageous in the case of home deodorizing products. Certain users of such devices at times do not desire to have guests know that such a product is in use. In these circumstances, the device may be removed from a prominent position that provides very effective delivery to a less prominent location. Because the device is repositionable, the same device may be returned to its earlier prominent position after the guests have departed.

As used herein, "repositionable" refers to the ability to be repeatedly adhered to and removed from a substrate without substantial loss of adhesion capability. Most preferably, the device of the present invention may be adhered to and removed from a painted wall substrate for thirty cycles with no more than 75% loss of peel adhesion. In another aspect, the present invention is removable from a substrate when it has been adhered to the substrate over a long period of time. Thus, preferably the adhesive used in the present invention does not develop excessive adhesion build-up over time.

To show repositionable adherence to the intended substrate, a device having a repositionable adhesive is applied to 20 pound white bond xerographic quality paper for 5 cycles, with the paper being adhered to the device for 24 hours for each cycle. Preferably, the device is held stationary and the bond paper is attached and removed from the paper at about 12 inches per minute and at 180 degree peel. After completion of the 5 cycles the device will support its own weight when suspended from a vertical or the underside of a horizontal white bond 20 pound xerographic quality paper substrate. Preferably, the device has sufficient shear and peel adhesion strength that it may be adhered to the underside of a white bond 20 pound xerographic quality paper substrate at any angle desired, including the underside of a substrate having a 45 degree angle position. The device has sufficient adhesion on its first application to a vertical white bond 20 pound xerographic quality paper substrate that it will hold its own weight (i.e. not fall off of the substrate) for at least 24 hours. Preferably, the device has sufficient adhesion that it will hold its own weight on its first application to a vertical white bond 20 pound xerographic quality paper substrate that it will hold its own weight for the term of effective delivery of the volatile material.

DETAILED DESCRIPTION OF THE INVENTION

Figure 1:
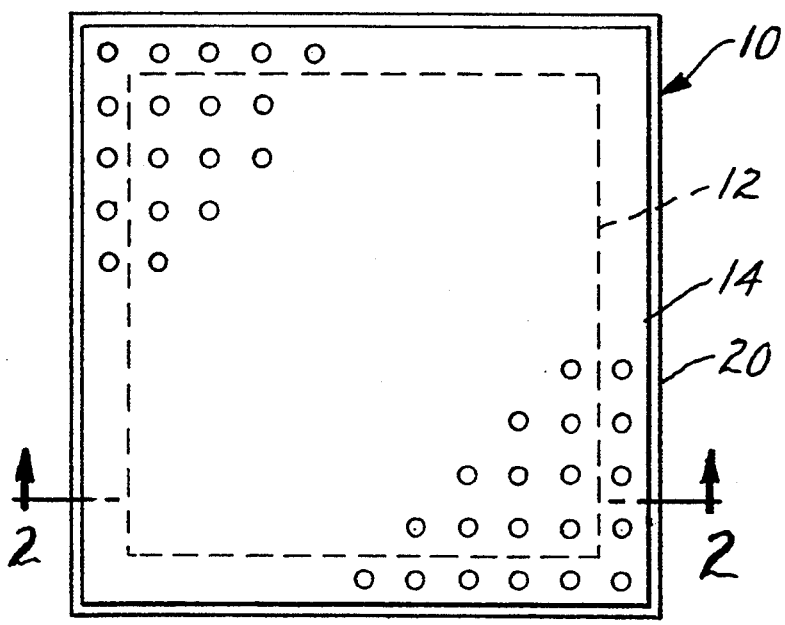
FIG. 1 is a plan view of an embodiment of the present invention wherein delivery of the volatile material is controlled through a cover sheet having a predetermined porosity.
Figure 2:
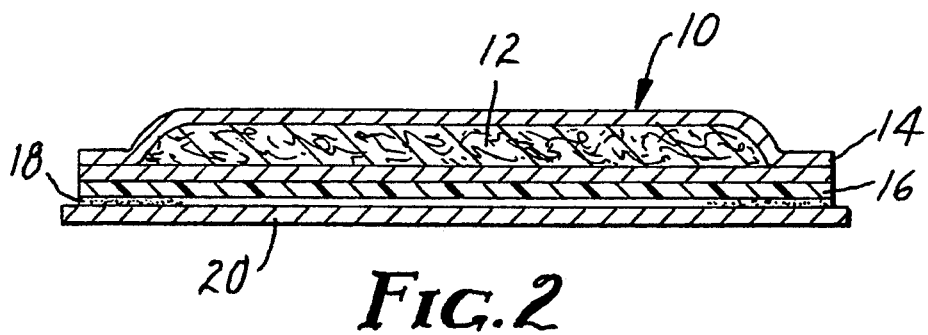
FIG. 2 is a cross-sectional view taken along line 2—2 of the embodiment of FIG. 1.

The material to be delivered by the devices described herein may be any volatile material that is desired to be delivered to a local atmosphere, such as a room. Preferably, the volatile material to be delivered is a fragrance suitable for room freshening or room deodorizing. The fragrance to be delivered may be of a single volatility, or may be a blend of compounds having different volatilities. Such blended fragrances are said to contain multiple "notes." Preferably, the fragrance blend comprises compounds having similar volatilities to provide a balanced fragrance throughout the fragrance delivery life of the product. As discussed below, the present devices may optionally comprise different delivery constructions for each note of a fragrance to provide a balanced fragrance throughout the fragrance delivery life of the product.

Devices for delivering volatile materials comprise a volatile material delivery layer, a support layer and a repositionable adhesive layer. The specific aspects of each of these elements are discussed below.

The volatile material delivery layer is selected from constructions that will hold and deliver volatile material over an appropriate time period desired for delivery of the material. One may, for example, desire to have a product that will provide very effective short term delivery of fragrance. In such a case, the volatile material delivery layer construction may be quite simple and consist only of a reservoir; that is, a material capable of holding a quantity of volatile material while allowing the material to dissipate over time. Examples of suitable reservoir materials include absorptive sheets, sponges, or pads of fabric capable of accommodating the volatile material. This material may be a nonwoven or woven fabric, such as nonwoven polypropylene webs. The reservoir may optionally be an open or closed cell sponge-like material. Alternatively, the reservoir may be a gel material, such as disclosed in U.S. Pat. No. 2,691,615 to Turner.

Volatile material may optionally be imbibed in or adsorbed on a solid, either in block or particulate form, that acts as a reservoir for the volatile material. Examples of such solids are talc, waxes and fatty alcohols, and polymeric particles either having interstices that provide a large amount of surface area to provide sites for adsorbing the fragrance oil on the particle or that are swellable by the fragrance oil. Polymer particles may, for example, be formed in the presence of incompatible materials that are later removed to provide particles having interstices.

Alternatively, the volatile material may be initially contained within one or more breakable capsules that are broken by the user only at the time that it is desired to initialize the release of the volatile material. Preferably, the breakable capsules are surrounded by material that will absorb and distribute the volatile material throughout an area having sufficient surface area to facilitate and enhance delivery of the volatile material.

The reservoir preferably is provided with sufficient volatile material that a continuous amount of volatile material is allowed to dissipate from the reservoir, but not so much that volatile material flows as a liquid from the device, regardless of the orientation of the device. Thus, a device preferably may be mounted in a vertical position without significant flow of volatile material to the lower edge of the device. Most preferably the device contains volatile material in a sufficiently limited quantity that one does not release liquid volatile material by squeezing the device with moderate pressure. It is desirable to avoid the possibility of generating liquid volatile material by squeezing because of the potential for harm or adverse physical reaction to, for example pets and children, when such volatile materials are incorporated and placed in a location where children or pets may encounter and misuse the present device.

The volatile material delivery layer preferably delivers the volatile material in a controlled manner. Most preferably the volatile materials delivered in a zero order or approaching a zero order delivery rate. The volatile material delivery layer may comprise the volatile material reservoir as disclosed above, on which is overlayed a diffusion rate controlling construction, such as a diffusion rate controlling membrane, high loft non-woven material, fabric cover sheet, provision for headspace to provide controlled diffusion of the volatile material away from the reservoir, and the like. For most effective zero order delivery, the volatile material is provided in a reservoir area that is capable of delivering the volatile material faster than the diffusion rate controlling aspect of the present construction.

In a controlled delivery device, the reservoir preferably provides highly efficient delivery of the volatile material. If the reservoir is highly absorbent, it may not release the volatile material quickly enough to provide rate limitation by the rate limiting layer. Thus, the reservoir preferably has a high surface area that will allow escape of the volatile material in a rapid manner. When the reservoir is a sponge-like structure, preferably it is of an open-cell foam rather than a closed-cell foam. When the reservoir is a non-woven or woven fabric pad, it is preferably prepared from fibers that do not absorb the volatile material. For example, polyethylene fibers are plasticized by fragrance oils, and therefore do not allow diffusion from the pad as readily as other fibers that are not plasticized by the volatile material. Fiber materials such as high density polypropylene and polyester are preferred for controlled delivery devices, because they provide good surface area and texture without absorbing the volatile material. More oleophobic and crystalline fibers are generally preferred. Additionally, these fibers are preferably selected from biodegradable materials.

The diffusion rate controlling membrane may be an essentially continuous film that allows permeation of the volatile material through the film, or may be a film imparted with perforations therethrough to allow vapor to be transmitted through the film at a controlled rate. Examples of such film material include those made from polyester, polyethylene, polypropylene, polyethylene terephthalate, polyurethane, and the like. These films are provided with perforations to allow controlled escape of the volatile material from the device. The size and number of holes provided in the diffusion rate controlling membrane is determined based on the affinity of the volatile material to the reservoir and the volatility of the volatile material. Where multiple notes of a fragrance are to be delivered, each note may be provided in its own section with a different diffusion rate controlling membrane having different size and/or number of holes to account for the different volatilities of the notes. Different amounts of components of a fragrance blend may also optionally be provided to adjust for the different volatilities of the fragrance notes. A balanced fragrance may thereby be delivered throughout the fragrance-delivery life of the device.

The diffusion rate of the volatile material may optionally be controlled by a fabric cover sheet, which inhibits free flow of the volatile material to the local atmosphere. Especially preferred are fabric cover sheets having a comparatively tight weave for good appearance and good control of volatile material dissipation. Satin fabrics, for example, provide excellent aesthetic appeal to the device.

The diffusion rate controlling membrane may optionally be a high loft non-woven material, which provides an interesting "fuzzy" appearance to the device. Devices having such a construction may additionally provide the benefit of delivery of a "bolus" of volatile material when air is forcibly circulated through the non-woven material by, for example, causing air to blow through the non-woven fibers or waving the device. Such devices are "traffic activated", in that the circulation of air through the non-woven cover provides a detectable additional release of fragrance above the continuously provided background level of fragrance. Preferably such non-woven covers have a void volume that is greater than 0.03 in.$^3$/in$^2$. void volume. While there is no upper limit per se in void volume of the non-woven cover sheet, a higher loft has less generally pleasing appearance and provides less marginal benefit in control of volatile material delivery. Preferably, a non-woven cover has a void volume between 0.15 and 0.3 in.$^3$/in$^2$.

Alternatively, the device may be provided with headspace between the reservoir and the local atmosphere to provide limited diffusion through saturated stagnant airspace.

The support layer used in the present device is a material suitable for providing support for both the volatile material delivery layer on one side and the repositionable adhesive layer on the other side. Preferably, the support layer is non-permeable to the volatile material to be delivered, thereby avoiding staining and bleed through of volatile material through the device to either reduce adhesion of the adhesive layer to the support layer, or damage of the intended substrate. The support layer is preferably compliant, thereby providing better conformance of the overall substrate to textured surfaces on which the device would be adhered. Examples of materials useful as support layers include polyethylene terephthalate films, ionomeric films (such as Surlyn TM film), etc. Preferably, polymeric films used as support layers have a thickness of no greater than about 5 mils.

The support layer may be substantially coextensive with the volatile material delivery layer, or may extend beyond the volatile material delivery layer to provide a margin on some or all edges. The margin of the support layer may serve to prevent transport of the volatile material by liquid flow to the substrate, thereby protecting the substrate from damage or staining by the volatile material. The margin may also serve as a tab means to provide easy removal of the device from the substrate. The margin may be trimmed in a shape that is the same or different from the shape of the volatile material delivery layer to provide a decorative effect.

As noted above, the device of the present invention may be repositionably adhered to any desired substrate. A repositionable adhesive may be provided through any of a number of recognized modes of providing a repositionable adhesive.

Ideally, depending on the substrate, the removable adhesive must provide sufficient tack (or quick stick) to quickly fix the adhesive to the desired substrate, sufficiently low peel strength to prevent damage of the surface when the adhesive is removed, and have the appropriate cohesive strength to control the transfer of adhesive to the substrate. Cold flow of the adhesive on a surface should be avoided, because this leads to an undesirable building of peel strength over time.

Preferably, the adhesive is an acrylate- or methacrylate-based adhesive system comprising infusible, solvent dispersible, solvent insoluble, inherently tacky, elastomeric copolymer microspheres as disclosed in U.S. Pat. No. 3,691,140. Alternatively, this adhesive composition may comprise hollow, polymer, acrylate, infusible, inherently tacky, solvent insoluble, solvent dispersible, elastomeric pressure-sensitive adhesive microspheres as disclosed in U.S. Pat. No. 5,045,569.

Preferably, the repositionable adhesive provided on the film comprises between about 60–100% by weight of hollow, polymeric, acrylate, inherently tacky, infusible, solvent-insoluble, solvent-dispersible, elastomeric pressure-sensitive adhesive microspheres having a diameter of at least 1 micrometer, and between about 0–40% by weight of a non-spherical polyacrylate adhesive. These hollow microspheres are made in accordance with the teaching of European Patent Application 371,635. The non-spherical polyacrylate adhesive may be any conventional pressure-sensitive adhesive. Examples of such adhesives are polymers made from the "soft" monomers such as n-butyl acrylate, isooctyl acrylate, or the like, or copolymers made from a soft component, such as isobutylene, n-butyl acrylate, isooctyl acrylate, ethyl hexyl acrylate, or the like; and a polar monomer such as acrylic acid, acrylonitrile, acrylamide, methacrylic acid, methyl methacrylate or the like. Non-spherical polyacrylate adhesives are commercially available, for example, as the Rohm and Haas Rhoplex TM line of adhesives. Preferably, the non-spherical polyacrylate adhesive is present in the repositionable adhesive at an amount of about 10–35% by weight. When the repositionable adhesive additionally comprises a non-spherical polyacrylate adhesive, improved anchorage of the total adhesive to the device is observed, resulting in less adhesive residue being left on the substrate after removal. Also, tacky microsphere-containing repositionable adhesives comprising non-spherical polyacrylate adhesive exhibit excellent shear adhesion properties, even for highly textured vertical surfaces. These advantageous adhesive properties are obtained without excessive adhesion to substrates such as painted walls that would result in peeling of the paint off of the wall when the film adhesive composite is removed.

Repositionable adhesives are also known in which microspheres contained in the adhesive are non-tacky. A disclosure of this type of adhesive is provided in U.S. Pat. No. 4,735,837 to Miyasaka.

A repositionable adhesive may be provided by addition of components to conventional adhesive formulations to modify their tack and flow characteristics. U.S. Pat. No. 4,599,265 (Esmay) discloses an adhesive having a high degree of cohesive strength that has low tack and maintains peelability from a variety of ordinary substrates. U.S. Pat. No. 4,737,559 (Kellen et al.) describes a PSA formulation in which the viscous flow, and resultant adhesion buildup, is controlled through the addition of a small amount of a free radically polymerizable photocrosslinker.

Another means for providing a repositionable adhesive through the reduction of the adhesive contact area is accomplished by the deposition of a discontinuous or patterned film on a backing. WO 85/04602 (Newing et al.) describes pressure-sensitive adhesive articles comprising a plurality of discontinuous adhesive segments in a pattern on at least a portion of at least one side of a carrier or backing, covering from about ten to about thirty percent of the total surface area of that carrier material. European Patent Application 276,557 (Fry) describes a repositionable pressure-sensitive sheet material comprising a sheet material bearing on one surface a discontinuous non-repetitive adhesive coating covering about 10 to about 85 percent of the surface in the form of individual adhesive islands. U.S. Pat. No. 4,889,234 (Sorenson et al.) discloses a discontinuous patterned adhesive label structure in which the level of adhesion is varied according to area of adhesive coverage on the label, the pattern in which the adhesive is coated, and the full coverage adhesive characteristics of the materials used. European Patent Application 279,579 (Tanuma et al.) describes pressure-sensitive adhesive sheets comprising, in one embodiment, a continuous adhesive layer having "irregular sections" (i.e., "... the pressure-sensitive adhesive layer is uneven ..."). The uneven adhesive layer, according to the application, is imparted through a variety of pressing, molding, and embossing methods.

Optimal repositionable adhesives used in the present device provide very little adhesive transfer to the substrate on which the device is adhered upon removal of the device. When the adhesive used contains tacky microspheres, the following test may be performed to determine the amount of microsphere transfer:

An area of coated sheet material is marked and observed using an optical microscope. The number of microspheres within the area are counted and this number designated "U". The marked area of the coated sheet is then adhered to Kromekote ™ paper, a commercially available paper for the printing industry, for a few seconds and then removed. The marked area is again observed with an optical microscope, and the number of microspheres remaining in the area are counted and this number designated "Z". Percent microsphere transfer is defined as 100 times the ratio of the difference between the number of microspheres initially present (in the marked area of the coated sheet) after coating and the umber of microspheres remaining in the marked area after each adhesion and removal from the paper substrate (Y-Z) to the number of microspheres initially present in the area just after coating.

$$\text{Percent transfer} = \frac{100(Y - Z)}{Y}$$

Preferably, the repositionable adhesive of the present invention has a microsphere transfer no more than 25%.

When the repositionable adhesive does not contain microspheres, a similar measurement may be performed by determining the weight of adhesive transferred to a substrate from a device having a known amount of adhesive coated thereon. As above, it is desirable to have no more than about 25% of adhesive transferred to the substrate, regardless of the nature of the adhesive.

Devices according to the present invention may be provided in a volatile material-impermeable envelope or other such sealed container. This sealed container prevents loss of volatile material before the intended use and also protects the device from being soiled in transit. Alternatively, a volatile material-impermeable cover sheet may be attached to the vapor-releasing parts of the present device, thereby preventing loss of volatile material. A separate support sheet would be provided with this embodiment to protect the repositionable adhesive from contamination with dust and the like prior to application to the intended substrate. The cover sheet may be adhered to the device through separate heat seal or adhesive means, or may be long enough to wrap around the entire device and adhere to part or all of the repositionable adhesive itself. Optionally, a portion of the adhesive may be exposed so that a plurality of devices may be stacked one atop the other, with each device repositionably adhering to the cover sheet of the successive device.

DETAILED DESCRIPTION OF THE DRAWING

Turning now to the drawing wherein like parts are represented by like numerals, FIG. 1 shows embodiment 10 of the present invention. Volatile material reservoir 12, shown here in phantom, contains volatile material to be dispersed to the atmosphere. Diffusion rate controlling sheet 14 envelopes volatile material reservoir 12, thereby controlling the egress of volatile material and the diffusion thereof. Support layer 16 provides fluid impermeable support for the volatile material reservoir 12 at diffusion rate controlling sheet 14, thereby protecting the surface of any substrate to which the embodiment 10 is to be attached from damage due to solvent effects of the volatile material. Repositionable adhesive layer 18 is coated on support layer 16, and is provided with release liner 20 for protection of adhesive layer 18 for delivery to the intended substrate.

In an alternative embodiment, the edge of embodiment 10 is curled away from contact with the substrate to which the embodiment is to be attached. This provides easy removal of the substrate by grasping the edge and further prevents wicking of volatile material around the edge of the embodiment, which would otherwise cause immediate contact of volatile material to the substrate.

Figure 3:
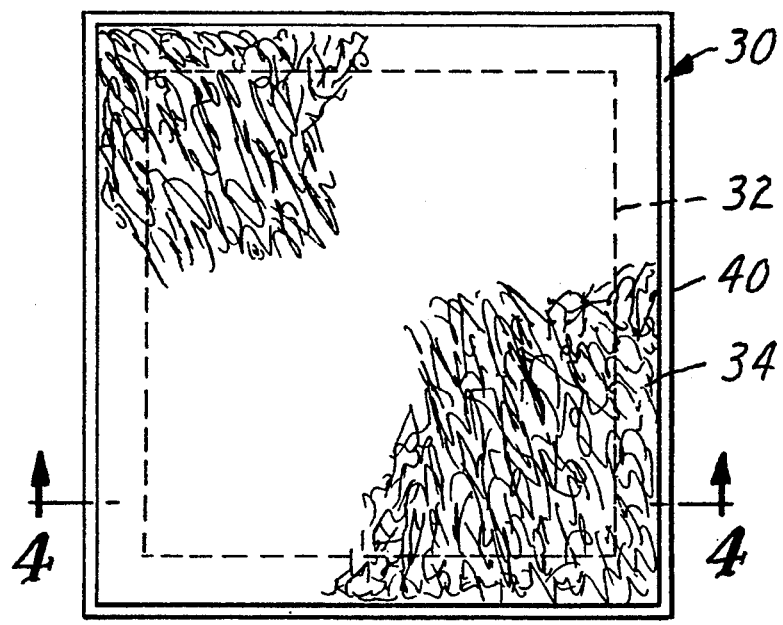
FIG. 3 is a plan view of an embodiment of the present invention wherein the diffusion of the volatile material is controlled through a fibrous pad cover.
Figure 4:
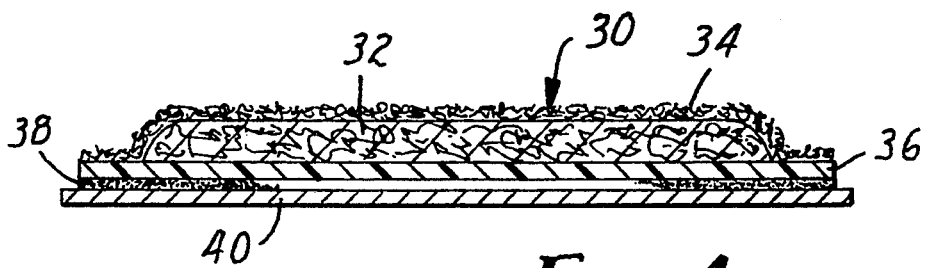
FIG. 4 is a cross-sectional view taken along the line 4—4 of the embodiment of FIG. 3.

Turning now to FIG. 3 and FIG. 4, embodiment 30 comprises volatile material reservoir 32, shown here in phantom. Fibrous cover material 34 provides controlled release of volatile materials, and additionally provides benefit through delivery of a "bolus" of additional fragrance upon circulation of air through the fibrous structure of the cover material. Support layer 36, repositionably adhesive layer 38, and release liner 40 are provided as above.

Figure 5:
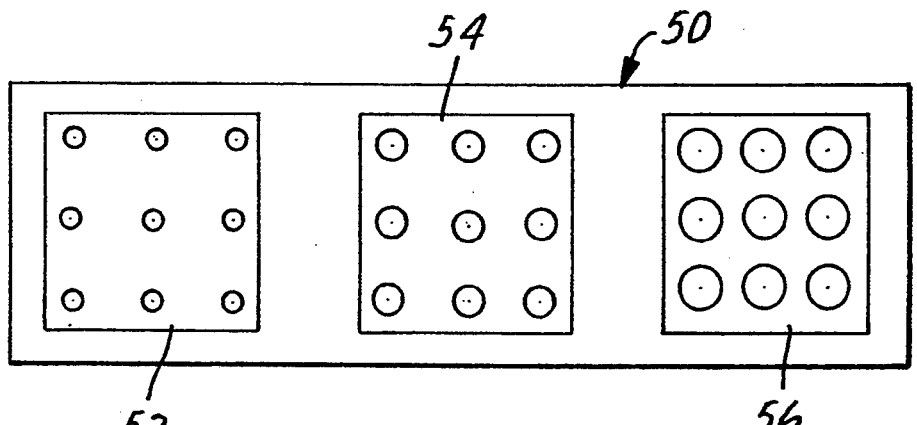
FIG. 5 is a plan view of an embodiment of the present invention comprising separate zones for delivery of different notes of a fragrance, wherein the notes have different volatilities.

FIG. 5 shows embodiment 50, which comprises regions having different permeabilities to volatile materials for delivery of different fractions of a fragrance, wherein the fractions have different volatilities. A highly volatile material of a fragrance is disposed within low permeability diffusion zone 52. A medium range volatility component is disposed within medium permeability diffusion zone 54, and a low volatility component is disposed within high permeability diffusion zone 56. Embodiment 50 provides comparatively uniform delivery of all three notes of the fragrance, providing a blend of fragrances that remains relatively constant in balance over time even though the notes have different volatilities.

Figure 6:
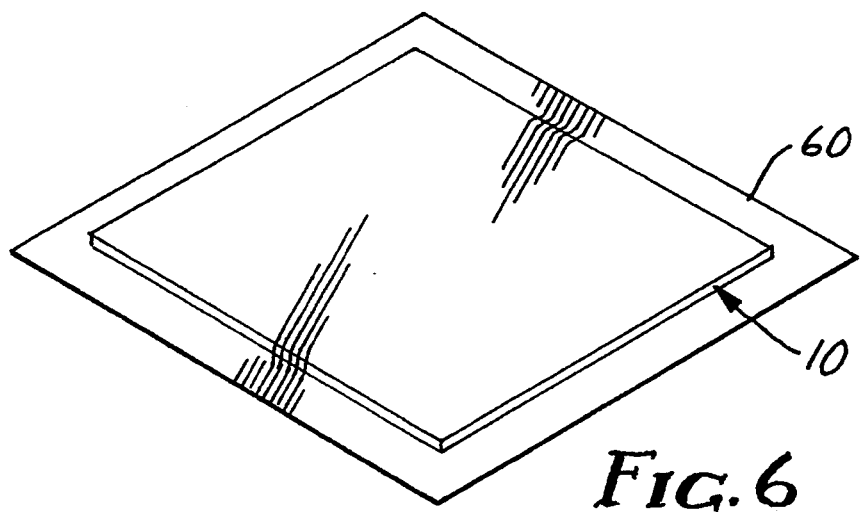
FIG. 6 is a perspective view of an embodiment to the present invention that is sealed in an impermeable envelope.

FIG. 6 shows a perspective view of embodiment 10 disposed within envelope 60. Envelope 60 is a non-permeable material.

These and other aspects of the invention are illustrated by the following examples which should not be viewed as limiting in scope.

EXAMPLE 1

A 4"×4" piece of Powersorb ™ P110 universal sorbant (commercially available from 3M) was provided with a moderate amount (approximately 0.15 g/in²) of a fragrance oil suitable for room air freshening applications. The pad was heat sealed between two pieces of Scotchpak ™ film (a polyethylene terephthalate and polyethylene terephthalate/isophthalate laminate commercially available from 3M) to form a sealed envelope. A repositionable transfer adhesive similar to #9415 3M Brand transfer adhesive was applied to one side, and 25 holes (nominal ⅛" diameter) were punched through the film of the other side of the envelope in an evenly spaced grid.

EXAMPLE 2

A 4"×4" piece of Powersorb ™ P110 universal sorbant was provided with a moderate amount (approximately 0.15 g/in²) of a fragrance oil suitable for room air freshening applications. The pad was heat sealed between a piece of Scotchpak ™ film and a layer of 4 mil porous high density polyethylene film having a 70% void volume and a Gurly number of 50 to form an envelope. A repositionable transfer adhesive similar to #9415 3M Brand transfer adhesive was applied to the Scotchpak ™ film side of the envelope. A layer of ⅜ inch thick thermal-bonding lofty polyolefin mat (approximately 0.004 g/m²) was adhered to the porous film side of the envelope.

EXAMPLE 3

A 4"×4" piece of Powersorb ™ P110 universal sorbant reservoir was provided with a moderate amount (approximately 0.15 g/in²) of a fragrance oil suitable for room air freshening applications, and a layer of ⅜ inch thick thermal-bondable lofty polyolefin mat (approximately 0.004 g/m²) was placed atop the reservoir. The pad was heat sealed between two pieces of Scotchpak ™ film to form an envelope. A repositionable transfer adhesive similar to #9415 3M Brand transfer adhesive was applied to the Scotchpak ™ film piece adjacent to the reservoir pad, and eight holes (nominal ⅛" diameter) were punched through the film on the side of the envelope adjacent the layer of packaging nonwoven fabric in an evenly spaced grid.

EXAMPLE 4

A 2½"×2½" piece of Powersorb ™ P110 universal sorbant reservoir was provided with a moderate amount (approximately 0.5 g/in²) of a fragrance oil suitable for room air freshening applications, and a layer of ⅜ inch thick thermal-bondable lofty polyolefin mat (approximately 0.004 g/m²) was placed atop the reservoir. A piece of Scotchpak ™ film was peripherally heat sealed to the polyolefin mat to form an envelope containing the reservoir. As a consequence of the heat-sealing operation, the Scotchpak ™ film was deformed to provide a depression accommodating the reservoir, with the margins of the support sheet elevated above the plane of the reservoir. The device was trimmed to 3"×3" to provide ¼" margins of the support sheet around the reservoir. A 2½"×2½" piece of repositionable transfer adhesive similar to #9415 3M Brand transfer adhesive was applied to the Scotchpak ™ film piece in the region generally corresponding to the location of the reservoir.

EXAMPLE 5

A reservoir was prepared using a polyester nonwoven fabric that is relatively rigid and embossed with hemispherical pits having a hemispherical radius of about 2 mm on 5 mm centers. The pits were filled with a fragrance bearing powder, which is octadecanol that has been melted and stirred with water and a small amount of surfactant, cooled while stirring to provide particles of about 20 micon size, filtered and dried and put in a jar with fragrance oil and allowed to take up fragrance oil to equilibration at a level of about 25 wt % perfume. A polyethylene support sheet having a thickness of about 1 mils was then laminated to the fabric, thereby trapping the particles in the hemispherical pits. A repositionable transfer adhesive similar to #9415 3M Brand transfer adhesive was then applied to the side of the support sheet opposite the nonwoven fabric.

EXAMPLE 6

A commercially available fragrancing device sold as the airwick ® stickup ® room freshener was modified by carefully removing the exposed permanent adhesive from the 1½ cm×1½ cm foam tape square provided on the back of the device. The back of the device other than the foam tape was masked, and an aerosol repositionable adhesive (ReMount ™ repositionable adhesive No. 6093, commercially available from 3M) was sprayed onto the foam tape in an amount sufficient to cover the tape. The device was adhered to a vertical glass substrate. Approximately 4½ hours later the device fell off of the glass. The same device was then applied to a latex-painted wall, where it remained attached for approximately 220 hours. This experiment shows that existing commercial devices may be modified to provide repositionable fragrance delivery devices effective for adhesion to certain substrates particularly compatible with the repositionable adhesive.

EXAMPLE 7

A commercially available fragrancing device sold as the airwick ® stickup ® room freshener was modified by removing the foam tape square provided on the back of the device and replacing it with a 2" diameter foam piece. The back of the device other than the foam was masked, and an aerosol repositionable adhesive (ReMount ™ repositionable adhesive No. 6093, commercially available from 3M) was sprayed onto the foam in an amount sufficient to cover the foam piece. The device was adhered to a vertical glass substrate. The device remained on the glass substrate in excess of 153 hours. This experiment shows that existing commercial devices may be modified by providing a surface area of the repositionable adhesive greater than the surface area of the original permanent adhesive, wherein the device has acceptable repositionable adhesion even to difficult substrates.

What is claimed:

1. A device for delivery of volatile materials comprising
   a) a volatile material delivery layer,
   b) a support layer, and
   c) a repositionable adhesive layer, wherein the repositionable adhesive layer is selected from a material such that said device may be adhered to and removed from white bond 20 pound xerographic quality paper at about 12 inches per minute and at 180 degree peel for 5 cycles with the paper being adhered to the device for 24 hours for each cycle without damaging said paper, wherein after completion of the 5 cycles the device will support its own weight when suspended from a vertical white bond 20 pound xerographic quality paper substrate.

2. The device according to claim 1, wherein said volatile material delivery layer delivers volatile material at approximately a zero order delivery rate.

3. The device according to claim 1, wherein said repositionable adhesive layer comprises tacky, elastomeric microspheres.

4. The device according to claim 1, wherein said repositionable adhesive layer is a pattern coated adhesive.

5. The device according to claim 1, wherein the repositionable adhesive layer is selected from a material such that said device may be adhered to and removed from white bond 20 pound xerographic quality paper at about 12 inches per minute and at 180 degree peel for 5 cycles with the paper being adhered to the device for 24 hours for each cycle without damaging said paper, wherein after completion of the 5 cycles the device will support its own weight when suspended from the underside of a horizontal white bond 20 pound xerographic quality paper substrate.

6. The device according to claim 1, wherein the repositionable adhesive layer is selected from a material such that said device has sufficient adhesion that it will hold its own weight on its first application to a vertical white bond 20 pound xerographic quality paper substrate for the term of effective delivery of the volatile material.

7. The device according to claim 1, wherein said volatile material delivery layer consists of a reservoir.

8. The device according to claim 7, wherein said reservoir is a nonwoven fabric pad.

9. The device according to claim 8, wherein said reservoir is a nonwoven polypropylene pad.

10. The device according to claim 1, wherein said volatile material delivery layer comprises a reservoir and an overlaid diffusion rate controlling construction.

11. The device according to claim 10, wherein said overlaid diffusion rate controlling construction is a diffusion rate controlling membrane.

12. The device according to claim 11 wherein said diffusion rate controlling membrane is a film material selected from the group consisting of polyester, polyethylene, polypropylene, polyethylene terephthalate and polyurethane, wherein said film material has been imparted with a plurality of perforations therethrough.

13. The device according to claim 10, wherein said overlaid diffusion rate controlling construction is a high loft non-woven material.

14. The device according to claim 10, wherein said overlaid diffusion rate controlling construction is a fabric sheet.

* * * * *